United States Patent
Maksimow et al.

(10) Patent No.: US 10,247,730 B2
(45) Date of Patent: Apr. 2, 2019

(54) METHOD FOR DETERMINING ACUTE RESPIRATORY DISTRESS SYNDROME (ARDS) RELATED BIOMARKERS, A METHOD TO MONITOR THE DEVELOPMENT AND TREATMENT OF ARDS IN A PATIENT

(71) Applicant: FARON PHARMACEUTICALS OY, Turku (FI)

(72) Inventors: Mikael Maksimow, Turku (FI); Marko Salmi, Turku (FI); Markku Jalkanen, Piispanristi (FI); Sirpa Jalkanen, Piispanristi (FI)

(73) Assignee: FARON PHARMACEUTICALS OY, Turku (FI)

( * ) Notice: Subject to any disclaimer, the term of this patent is extended or adjusted under 35 U.S.C. 154(b) by 0 days.

(21) Appl. No.: 14/767,464

(22) PCT Filed: Jan. 22, 2014

(86) PCT No.: PCT/FI2014/050051
§ 371 (c)(1),
(2) Date: Aug. 12, 2015

(87) PCT Pub. No.: WO2014/125164
PCT Pub. Date: Aug. 21, 2014

(65) Prior Publication Data
US 2015/0377885 A1    Dec. 31, 2015

(30) Foreign Application Priority Data
Feb. 14, 2013 (FI) .................................... 20130049

(51) Int. Cl.
| | | |
|---|---|---|
| A61K 38/21 | (2006.01) | |
| G01N 33/68 | (2006.01) | |
| G01N 33/573 | (2006.01) | |
| G01N 30/90 | (2006.01) | |

(52) U.S. Cl.
CPC ......... *G01N 33/573* (2013.01); *A61K 38/215* (2013.01); *G01N 33/6884* (2013.01); *G01N 33/6893* (2013.01); *G01N 30/90* (2013.01); *G01N 2333/70596* (2013.01); *G01N 2333/916* (2013.01); *G01N 2800/125* (2013.01); *G01N 2800/52* (2013.01); *G01N 2800/60* (2013.01)

(58) Field of Classification Search
CPC ............... A61K 38/215; G01N 33/573; G01N 33/6863; G01N 33/6893; G01N 2800/00; G01N 2800/125; G01N 2800/52; G01N 2333/916; G01N 2333/70596
See application file for complete search history.

(56) References Cited

U.S. PATENT DOCUMENTS 6,190,872 B1    2/2001    Slotman

FOREIGN PATENT DOCUMENTS

| WO | 03/056896 A2 | 7/2003 |
| WO | 2006/039819 A1 | 4/2006 |
| WO | 2008/034621 A2 | 3/2008 |
| WO | 2009/053523 A1 | 4/2009 |

OTHER PUBLICATIONS

Eckle, T., et al. Identification of ectonucleotidases CD39 and CD73 in innate protection during acute lung injury. J. Immunol., 2007, vol. 178, p. 8127-8137.*
Lin, W-C, et al. Prediction of outcome in patients with acute respiratory distress syndrome by bronchoalveolar lavage inflammatory mediators, Experimental Biology and Medicine, 2010, vol. 235, p. 57-65.*
L.R. Bisset, et al. Chemokines and their receptors in the pathogenesis of allergic asthma: progress and perspective. Current Opinion in Pulmonary Medicine, 2005, vol. 11, p. 35-42.*
Fremont, R.D. et al., "Acute Lung Injury in Patients With Traumatic Injuries: Utility of a Panel of Biomarkers for Diagnosis and Pathogenesis," The Journal of Trauma, May 2010, vol. 68, No. 5, pp. 1121-1127.
The ARDS Definition Task Force: Acute Respiratory Distress Syndrome,The Berlin Definition, JAMA 2012, vol. 307, No. 23, pp. 2526-2533.
Frenzel, J. et al., "Outcome Prediction in Pneumonia Induced ALI/ARDS by Clinical Features and Peptide Patterns of BALF Determined by Mass Spectrometry," PLOS ONE, Oct. 2011, vol. 6, No. 10, e25544, pp. 1-12.

(Continued)

*Primary Examiner* — Robert S Landsman
*Assistant Examiner* — Bruce D. Hissong
(74) *Attorney, Agent, or Firm* — Rothwell, Figg, Ernst & Manbeck, P.C.

(57) ABSTRACT

This invention concerns methods for monitoring the development of and for treatment of ARDS in a patient. The method for monitoring the development of ARDS is based on comparing the level or activity of the biomarkers obtained in a sample drawn at a later point of time to the levels or activities of the same biomarkers in a sample drawn at a previous point of time. A favorable change in the level or activity of a certain biomarker represents a regression of the disease (recovery of the patient), and, conversely, an adverse change in the level or activity of a certain biomarker represents a worsening of the disease. If, for example, the level or activity for one or more of the biomarkers monitored discontinues to show a favorable change or starts to show an unfavorable change, the treatment of the patient is enhanced by administering a therapeutically active agent useful in the treatment of ARDS. The invention concerns further a method for simultaneous determination of a multiple of biomarkers in a sample from a patient, wherein said biomarkers are related to ARDS. The level or the activity of the biomarkers is determined. The invention also concerns a diagnostic kit useful for carrying out the method, particularly a kit comprising a chip, such as a microarray suitable for use in biochip technology.

15 Claims, 7 Drawing Sheets

(56) References Cited

OTHER PUBLICATIONS

Bellingan, G.J. et al., "Serum Cd73 Activity, An Enzyme Involved in Endothelial Barrier Function, Increases Following Fp-1201 Treatment of Ali/ards Patients," American Journal of Respiratory and Critical Care Medicine, 2011, vol. 183, p. A1680.
Finnish Search Report dated Nov. 14, 2013, National Board of Patents and Registration of Finland, Finnish Application No. 20130049, 3 pages.
International Search Report dated Jun. 9, 2014, International Application No. PCT/FI2014/050051, 8 pages.
Matthay et al., "Therapeutic Potential of Mesenchymal Stem Cells for Severe Acute Lung Injury", CHEST, 138, Oct. 4, 2010, 956-972.
English translation of Office Action Cited in Japanese Patent Application No. 2015-557488 dated Sep. 5, 2017, 5 pgs.
Bellinggan et al., "The effect of intravenous interferon-beta-1a(FP-1201) on lung CD73 expression and on acute respiratory distress syndrome mortality: an open-label study", thelancet.com/respiratory, Feb. 2014, vol. 2, pp. 98-107.

\* cited by examiner

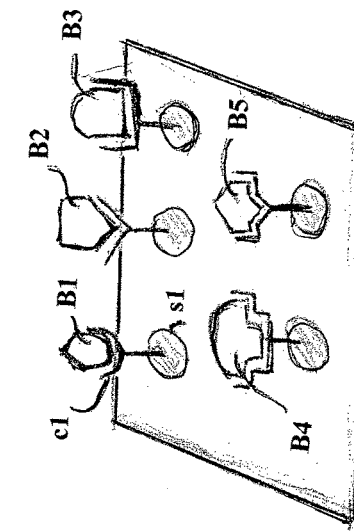
FIG. 1C
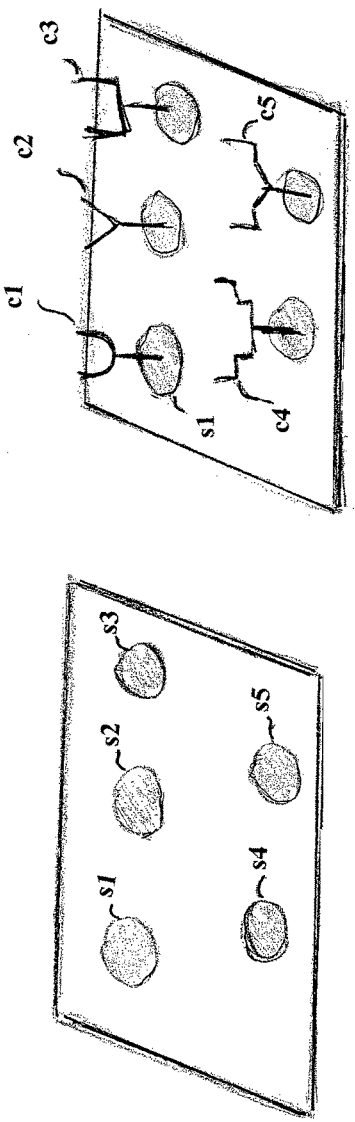
FIG. 1B
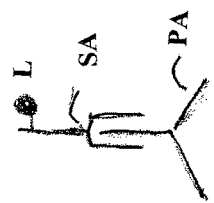
FIG. 2
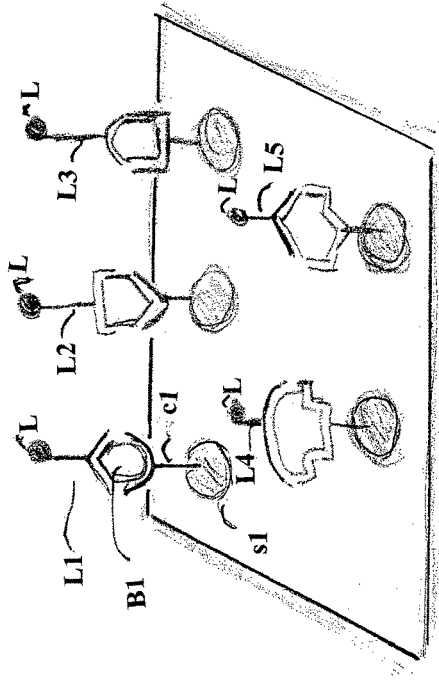
FIG. 1A
FIG. 1D

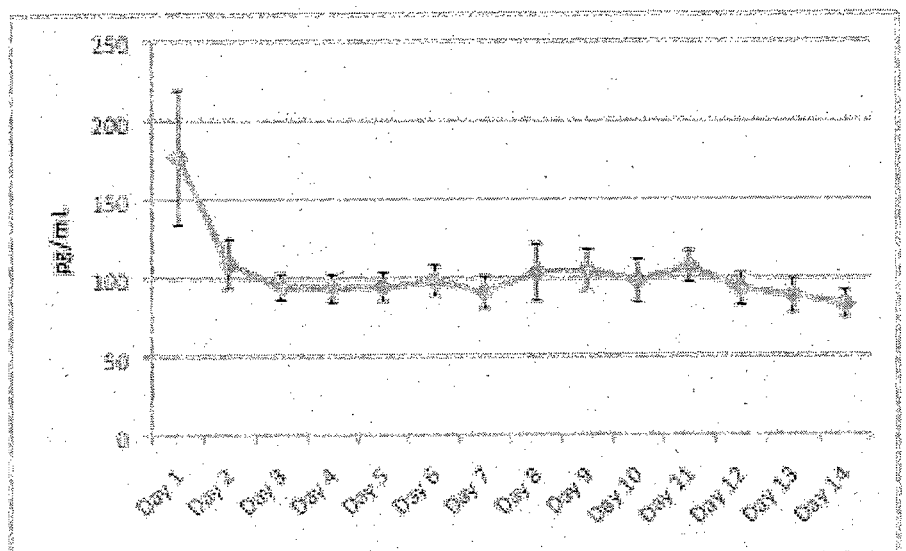
FIG. 4a (IL-1ra)
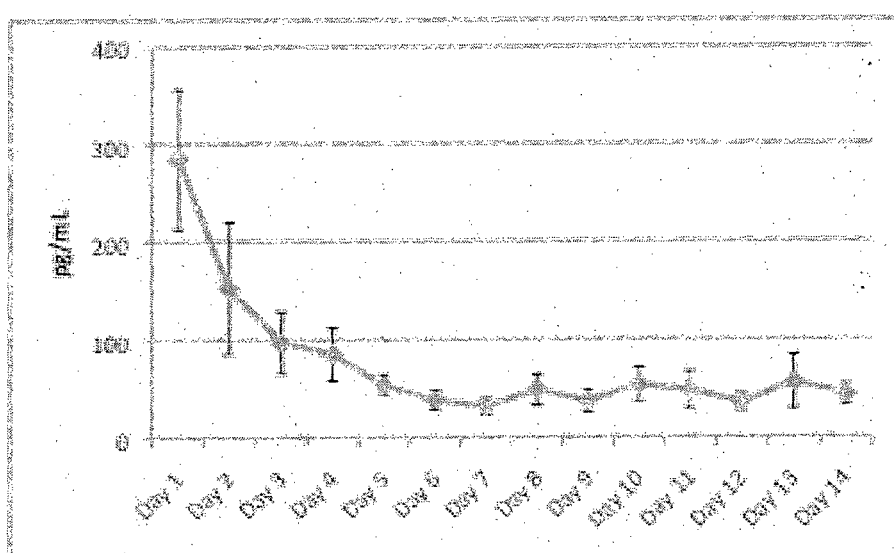
FIG. 4b (IL-6)

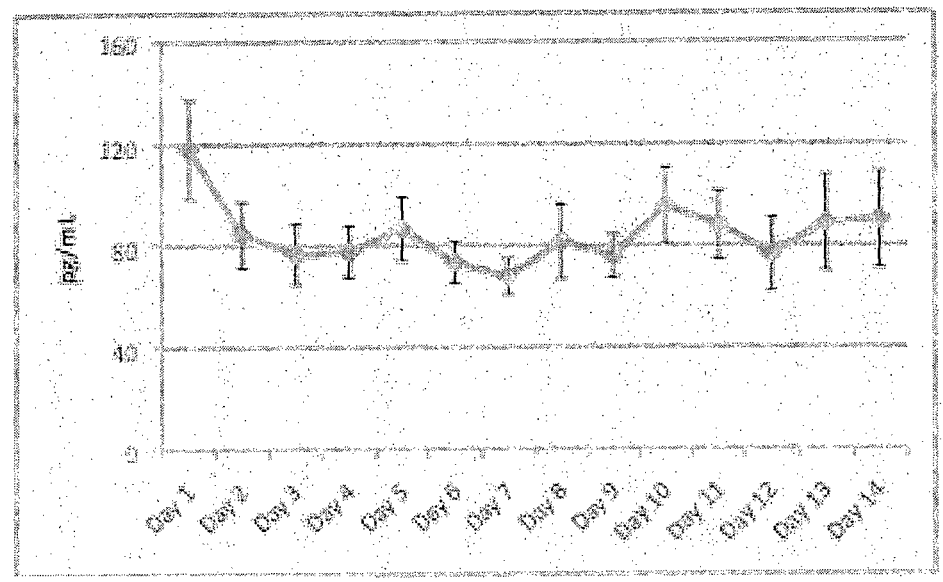
FIG. 4c (Il-8)
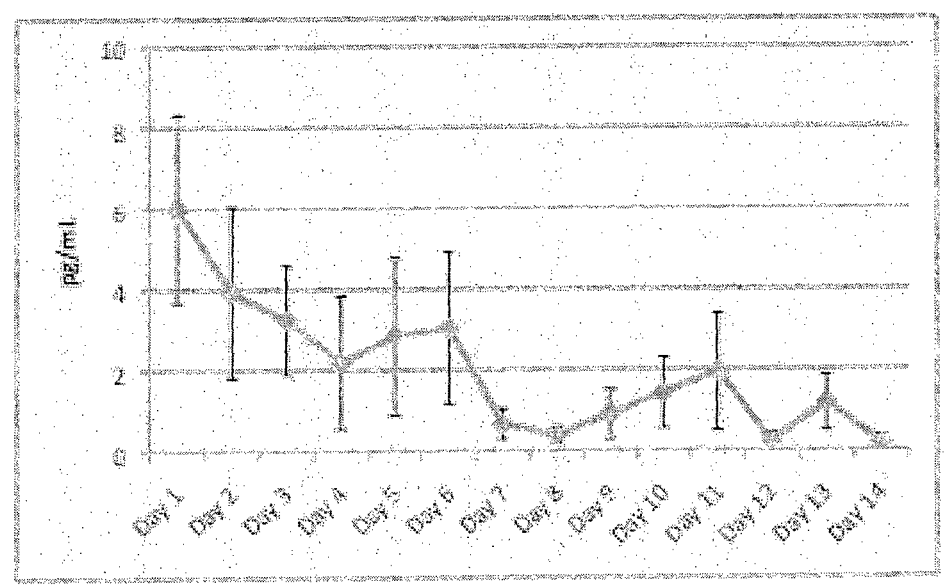
FIG. 4d (IL-15)

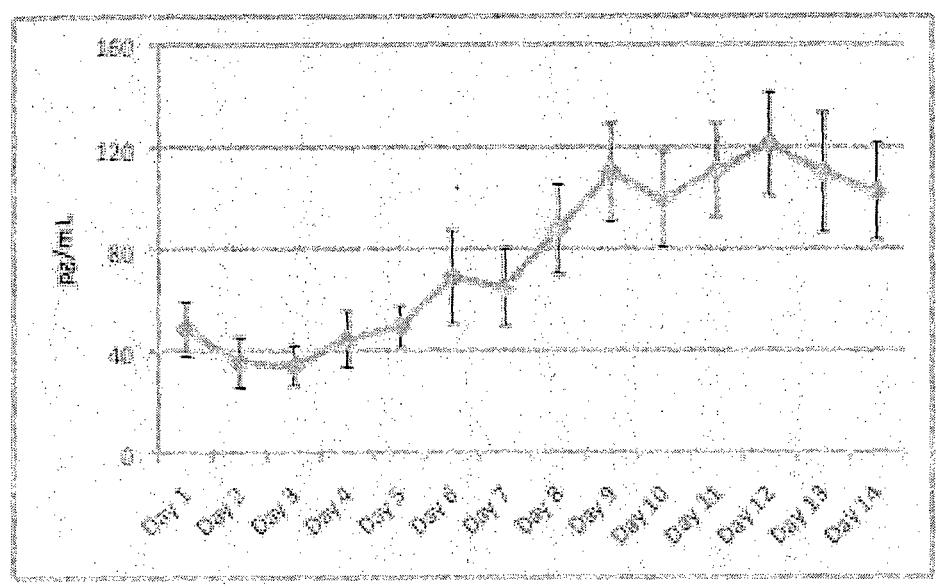
FIG. 4e (Eotaxin)
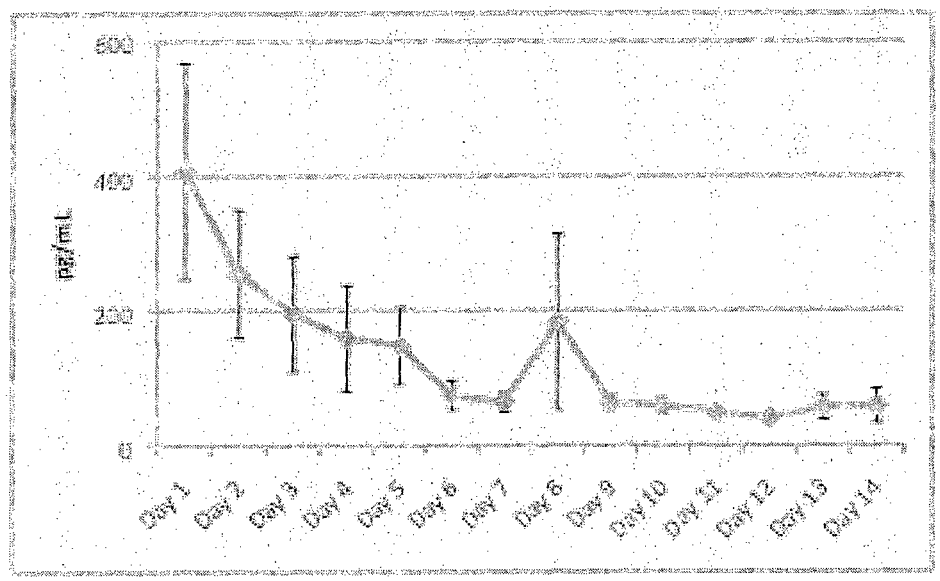
FIG. 4f (MCP-1)

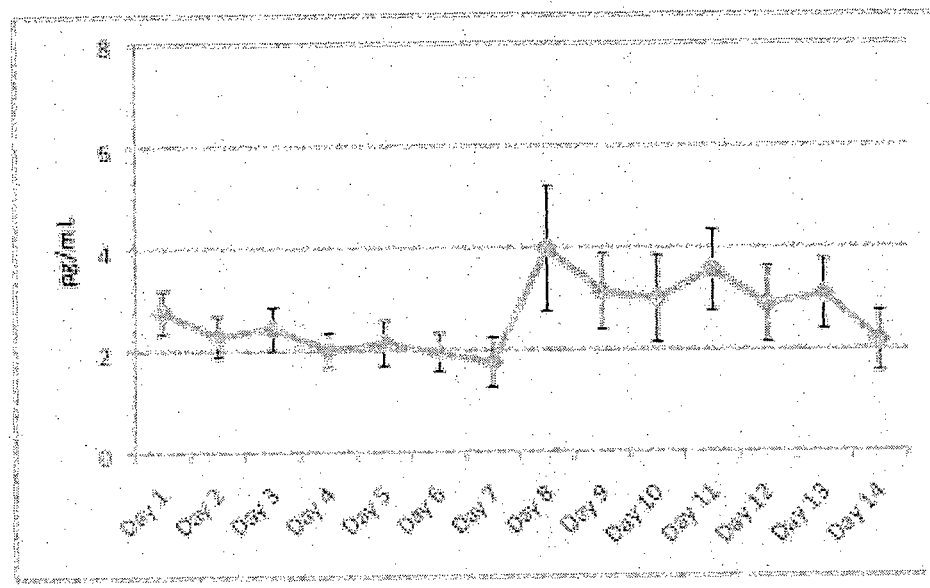
FIG. 4g (MIP-1a)
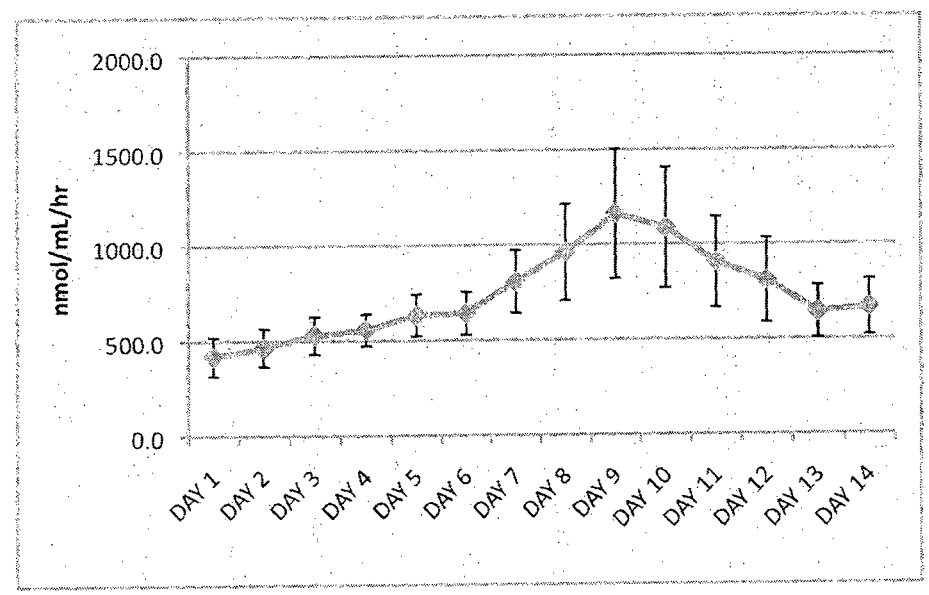
FIG. 4h (CD73)

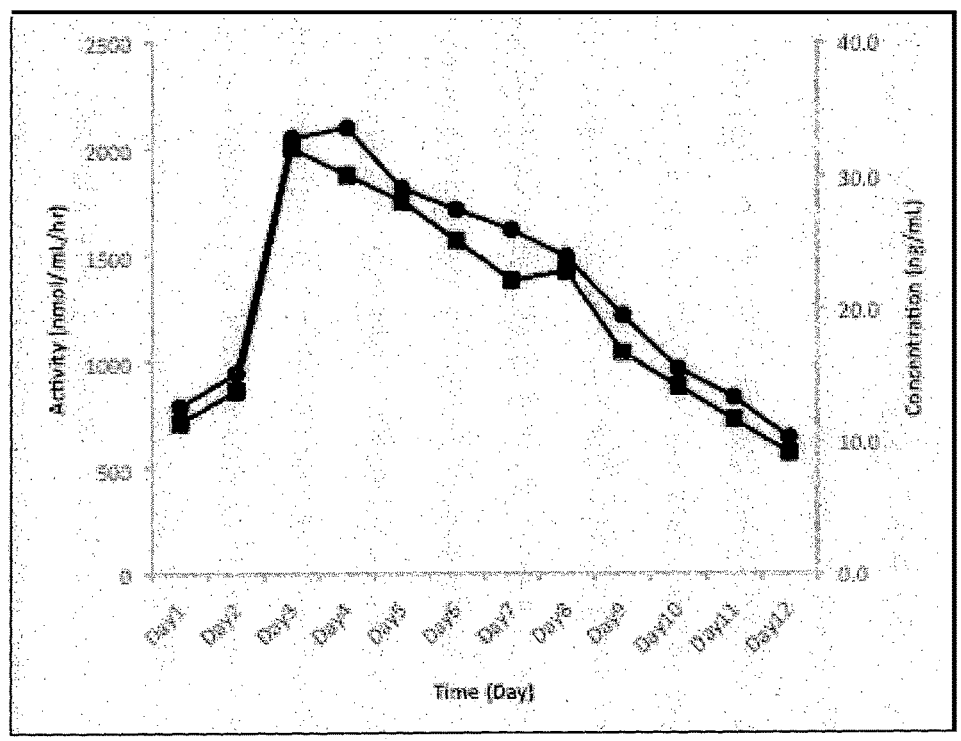
FIG. 5 (CD73)

METHOD FOR DETERMINING ACUTE RESPIRATORY DISTRESS SYNDROME (ARDS) RELATED BIOMARKERS, A METHOD TO MONITOR THE DEVELOPMENT AND TREATMENT OF ARDS IN A PATIENT

CROSS-REFERENCE OF THE RELATED APPLICATION

The present application is a § 371 U.S. National Phase Entry of International Application No. PCT/FI2014/050051 filed on 22 Jan. 2014, which in turn claims priority to Finnish patent application No. 20130049 filed on 14 Feb. 2013. Each application is incorporated herein by reference in its entirety.

FIELD OF THE INVENTION

This invention concerns methods for monitoring the development of and for treatment of acute respiratory distress syndrome (ARDS) in a patient. The method for monitoring the development of ARDS is based on comparing the level or activity of the biomarkers obtained in a sample drawn at a later point of time to the levels or activities of the same biomarkers in a sample drawn at a previous point of time. A favourable change in the level or activity of a certain biomarker represents a regression of the disease (recovery of the patient), and, conversely, an adverse change in the level or activity of a certain biomarker represents a worsening of the disease. If, for example, the level or activity for one or more of the biomarkers monitored discontinues to show a favourable change or starts to show an unfavourable change, the treatment of the patient is enhanced by administering a therapeutically active agent useful in the treatment of ARDS.

The invention concerns further a method for simultaneous determination of a multiple of biomarkers in a sample from a patient, wherein said biomarkers are related to ARDS. The levels or the activities of the biomarkers are determined. The invention also concerns a diagnostic kit useful for carrying out the method, particularly a kit comprising a chip, such as a microarray suitable for use in biochip technology.

BACKGROUND OF THE INVENTION

The publications and other materials used herein to illuminate the background of the invention, and in particular, cases to provide additional details respecting the practice, are incorporated by reference.

Multiplex assays, i.e. methods for simultaneous detection or quantification of a multiple of analytes in a sample are as such well known. Such assays are assays that simultaneously measure multiple analytes in a single run. Multiplex assays can be classified based on how many analytes can be measured per assay: the amount of analytes range from a few (at least two) up a very high number. The commercial multiplex assays are typically designed for simultaneous detection of up to about 50 analytes. These methods can be used for analyses of nucleic acids and proteins, such as antibodies. Also carbohydrates and other chemical compounds can be measured.

The multiplex methods can be carried out in many alternative ways.

As an example can be mentioned a microarray which is a 2D array on a solid support that simultaneously assays a large number of biological analytes. In a protein microarray such as an antibody microassay different antibodies have been affixed on a solid support at separate locations in a predetermined pattern. These antibodies are used as capture molecules capable of capturing analytes (proteins) present in a sample.

As an example of a commercially available assay can be mentioned Luminex® xMAP Technology, which is a bead-based assay performed directly in a microtiter plate. Each assay contains a mixture of different microspheres (bead mix), where each bead type is defined by an individual fluorescent color tone for analyte classification and carries a specific capture reagent such as specific proteins (antibodies) on its surface. During incubation of the bead mix with the patient sample complementary reaction partner (antigens) bind to the capture antibodies on the micro-spheres. In a second incubation step the bound antigens are detected with labelled antibodies bearing a specific fluorescent marker. The amount of bound analyte (antigen) correlates directly to the fluorescent intensity of the detecting antibody allowing the quantification of analytes. The classification of the beads and the quantification of the antigens are performed with the Luminex analysis system, which is based on the technology of flow cytometry using two different lasers.

The use of multiple sequential biomarkers for diagnosis and prognosis of diseases has also been suggested.

Chirag R Parikh et al., Crit Care Med 2008 Vol. 36, No. 4 (Suppl); p S159-S165, suggests the use of multiple sequential biomarkers for assessing the duration of AKI (acute kidney injury) and for predicting overall prognosis with respect to dialysis requirement and mortality. The biomarkers were NGAL (neutrophil gelatinase-associated lipocalin) and cystatin C in a plasma panel and NGAL, IL-18 (interleukin-18) and KIM-1 (kidney injury molecule-1) in a urine panel.

O Beran et al., Eur J Clin Microbiol Infect Dis (2009) 28: 793-799 describes sequential analysis of biomarkers such as IL-6 (interleukin-6), IL-1ra (interleukin-1 receptor antagonist), IL-1beta (interleukin-1beta), IL-8 (interleukin-8), MIP-1beta (macrophage inflammatory protein-1beta) and MCP-1 (monocyte chemoattractant protein-1) and their correlation with IMD (invasive meningococcal disease) and the severity thereof.

WO 2009/053523, Faron Pharmaceuticals Oy, discloses that CD73 is a useful biomarker for monitoring the development of inflammatory diseases, in particular SIRS (systemic inflammatory response syndrome), ALI (acute lung injury), ARDS and MOF (multi-organ failure) in a patient. Tissue fluid samples were drawn from the patients at different points of time and the CD73 activity in the samples was determined. An increased level of CD73 activity was found to correlate with regression of the disease.

So far, nobody has suggested the use of multiple sequential biomarkers for monitoring the development of ARDS in a patient. Particularly, nobody has suggested the use of a set of biomarkers consisting of or including CD73 and IL-6 for this purpose.

SUMMARY OF THE INVENTION

The aim of this invention is to provide methods and means to follow the severity of ARDS during the treatment period of this condition. Usually the ARDS patients receive the best possible intensive care but more importantly, the use of biomarkers to predict any pharmacological treatment is becoming very valuable asset to evaluate the efficacy of the treatment. One such treatment is Traumakine® FP-1201 (interferon beta), which has shown to reduce mortality of ARDS patients. By having valuable predictive data about the patient's condition the ICU doctor can optimize the care of the patient.

Thus, in one aspect, the invention concerns a method for simultaneous determination of a multiple of ARDS related biomarkers in a sample drawn from a patient, wherein one of the biomarkers is CD73 protein. According to the invention, said method comprises the steps of i) quantifying the levels of the biomarkers in said sample by subjecting the sample to binders recognizing the biomarkers, or ii) determining the activities of the biomarkers in said sample by using thin layer chromatography or by subjecting said sample to substrates for the biomarkers, and monitoring the change of said substrates.

In another aspect, this invention concerns a diagnostic kit for use in a bioaffinity assay method for simultaneous determination of a multiple of ARDS related biomarkers in a sample drawn from a patient, wherein the number of biomarkers including CD73 and additional biomarkers is at least 2, preferably 2-50, most preferably 2-8. According to the invention said kit comprises a set of capture binders immobilised to a solid support or capable of being immobilised to a solid support, wherein each capture binder is specific for a certain biomarker to be determined, and a set of labelled bioaffinity components, wherein each such labelled bioaffinity component has a bioaffinity specific for a certain immobilised biomarker, or wherein each such labelled bioaffinity component has an ability to compete for the binding site with a certain immobilised biomarker.

In a third aspect this inventions concerns a method for monitoring the development of ARDS in a patient, wherein at least 2, preferably 2 to 50, most preferably 2 to 8 ARDS-related biomarkers in samples drawn from a patient at different points of time have been determined, and wherein one of the biomarkers is CD73 protein, said method being based on comparing the levels or activities of the biomarkers obtained in a sample drawn at a later point of time to the levels or activities of the same biomarkers in a sample drawn at a previous point of time, wherein a favourable change in the level or activity of a certain biomarker represents a regression of the disease, and wherein an adverse change in the level or activity of a certain biomarker represents a worsening of the disease.

In a fourth aspect this invention concerns a method for the treatment of a patient suffering from ARDS by administering to the patient a therapeutically active agent effective in the treatment of ARDS, wherein the administration is started as soon as one or more of the biomarkers used in monitoring of the development of ARDS according to this invention
    discontinues to show a favourable change, or
    starts to show an unfavourable change.

BRIEF DESCRIPTION OF THE DRAWINGS

FIG. 1A shows a support with spots capable of binding capture binders,

FIG. 1B shows the support of FIG. 1A onto which capture binders are immobilised, FIG. 1C shows the support of FIG. 1B onto which biomarkers to be determined have been immobilised to the capture binders, FIG. 1D shows the support of FIG. 1C onto which labelled binders have been immobilised to the biomarkers to be determined, FIG. 2 shows a labelled antibody comprising an assembly of primary antibody directed to the biomarker and a secondary antibody, which bears the label and binds to the Fc region of the primary antibody.

FIGS. 4a to 4h show the level or activity of eight biomarkers as function of time for a group of patients recovering from ALI or ARDS (FIGS. 4a-4g show the level; FIG. 4h show the activity).

FIG. 5 shows both the activity and level (concentration) of soluble CD73 as function of time for one patient recovering from ALI or ARDS as an example.

Soluble CD73 activity (•, left y-axis) and soluble CD73 concentration (•, right y-axis) were measured from aliquots of the same samples. FIG. 5 shows that activity and concentration measurements are comparable. One can see that CD73 (FIG. 5) and IL-6 (FIG. 4b) values show a dramatic change in the plasma concentrations, which indicate favourable changes.

DETAILED DESCRIPTION OF THE INVENTION

Figure 3:
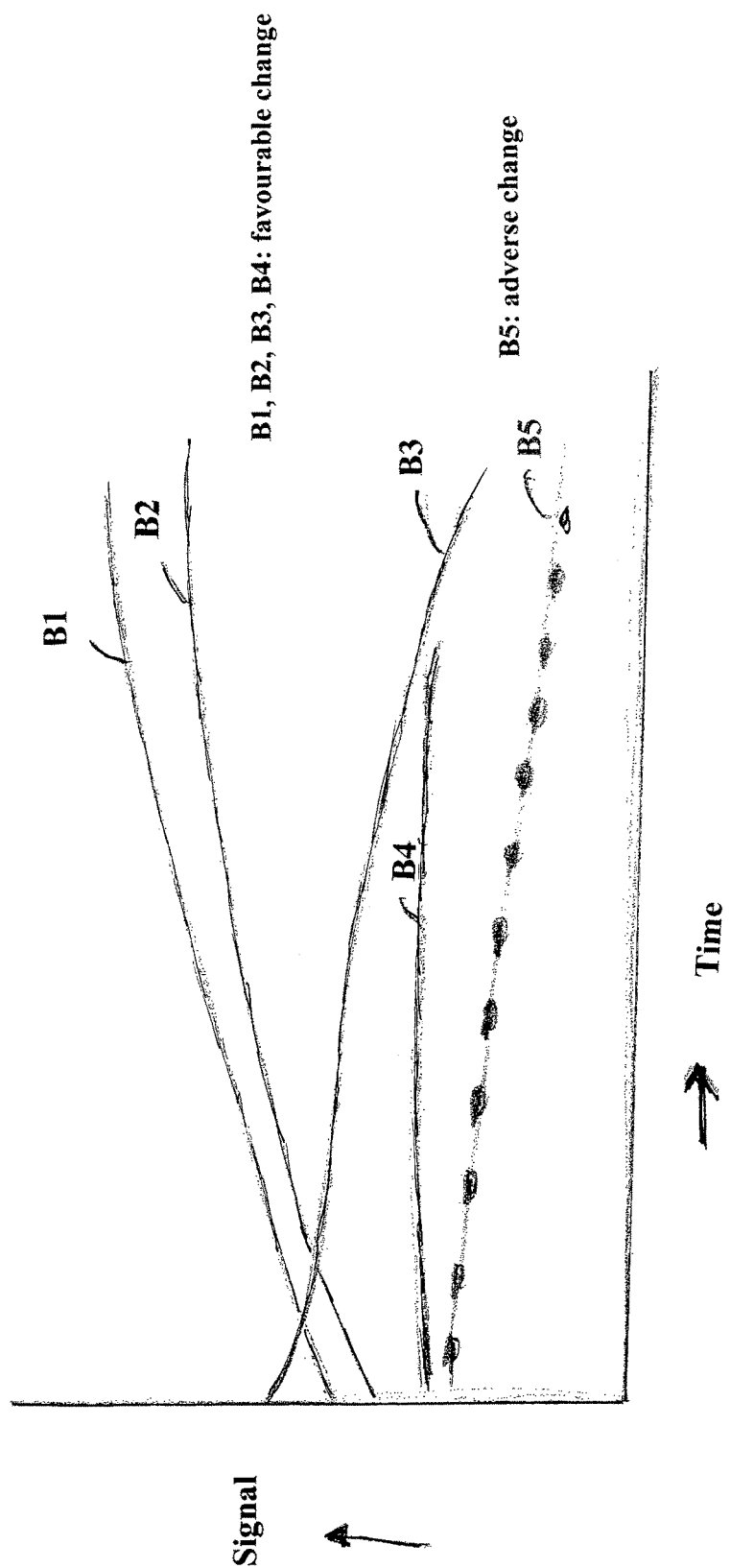
FIG. 3 shows s set of curves for the levels of measured biomarkers as function of time. The whole lines for B1 to B4 indicate that the changes over time are favourable. The dotted line for B5 means that the decrease of its level represents an adverse change.

The sample can be any tissue fluid, which bathes and surrounds the cells. The term includes, for example, blood plasma, serum, whole blood, lympha, urine, exudates (pleural, peritoneal) and cerebrospinal fluid.

The ARDS related biomarkers refer to a set of biomarkers present in a sample derived from the patient. The set of biomarkers comprise at least two, preferably two to eight biomarkers, particularly about five biomarkers, of which one is CD73 protein. As examples of other biomarkers can be mentioned cytokines, which are proteins or peptides used in organisms as signalling compounds. The cytokines include, for example, interferons, interleukins, particularly IL-6, chemokines such as eotaxins. As examples of other suitable biomarkers can be mentioned CRP (C-Reactive Protein) and other pentraxins.

Preferably, the biomarkers are selected from the group including the following: IL-1β, IL-1ra, IL-2, IL-4, IL-5, IL-6, IL-7, IL-8, IL-9, IL-10, IL-12 (p'70), IL-13, IL-15, IL-17A, Basic FGF, Eotaxin, G-CSF, GM-CSF, IFN-γ, IP-10, MCP-1, MIP-1α, MIP-1β, PDGF-BB, RANTES, TNF-α, VEGF, IL-1α, IL-2Rα, IL-3, IL-12 (p'70), IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL, CD73, CRP, Neopterin, MxA, and beta-2-microglobulin.

A particularly preferred set of biomarkers include CD73 and IL-6, either these two biomarkers, or these two biomarkers in combination with one or a few additional biomarkers. In particular, such additional biomarker is selected from the group consisting of IL-8, IL-15, Eotaxin, MPC-1, MIP-1a and IL-1ra. Preferably, such set of biomarkers comprises three to eight of the biomarkers CD73, IL-6, IL-8, IL-15, Eotaxin, MPC-1, MIP-1a and IL-1ra, provided that at least two of them is CD73 and IL-6. A particularly preferred set comprises all the eight biomarkers CD73, IL-6, IL-8, IL-15, Eotaxin, MPC-1, MIP-1a and IL-1ra.

In one alternative, the activities of the biomarkers are determined. This is carried out, for example, either by using thin layer chromatography or by subjecting the sample to substrates for the biomarkers, and monitoring the change of said substrates.

The activity of the biomarkers can, for example, be measured using thin layer chromatography according to published protocols. The activity can be also measured using any enzymatic assay that measures the conversion of a suitable substrate. For example, for CD73 the activity can be measured by conversion of AMP or another purine mononucleotide that can be used as a CD73 substrate, into the corresponding nucleoside. For example, the assay can be based on conversion of radioactively or fluorescently labelled substrates. Detection methods can rely on the quantification of the decrease in a substrate concentration, or an increase in the product concentration or the release of the phosphate group. The CD73 dependence of the reaction can be determined by performing the assay in the presence and absence of a known CD73 inhibitor, such as AMPCP.

Generally, reporter cell lines for activity measurements are such genetically engineered cell lines in which a compound or molecule (i.e. the biomarker) of interest specifically induces a reporter gene expression. Such reporter gene expression can result in light production or in another measurable function that is quantifiable. The quantification of the reporter gene activity can then be used to calculate the activity and/or level of the compound or molecule of interest.

Monoclonal antibodies specific for the biomarkers mentioned above are described in the literature and they are available from many commercial sources such as Bio-Rad Laboratories, Inc., Jena Bioscience GmbH and Sino Biological, Inc.

To qualify for an "ARDS related biomarker", said biomarker shall have been found to correlate to the status of the ARDS disease so that an altered level of the biomarker over time indicates the change of the status of the disease. Those biomarkers with strongest associations will be combined to the ARDS biomarker panel. For example, an increasing level of CD73 from one point of time to a later point of time indicates the efficiency of a treatment with a therapeutically active agent and consequently, the regression of ARDS. For CRP, however, an increasing level indicates the worsening of the disease. It is therefore important to first study each suitable biomarker to found out whether an increase or decrease of its level is a favourable change or an adverse change with respect to the disease status.

The "bioaffinity assay" can be either an immunoassay if the biomarkers are proteins. Alternatively, it refers to a hybridising assay if the biomarkers are nucleic acids.

The "binder" (capture binder or labelled binder) refers to antibodies or the like (for example, affibodies and aptamers) when the biomarkers to be determined are proteins or peptides. If the biomarkers are nucleic acids the binders are preferably oligonucleotides.

The term "solid support" is, for example, a microsphere or bead, which bears a label. Alternatively, the solid support refers to a microtiter plate or a chip. Preferably, the solid support is a chip, such as a microarray, suitable for use in a biochip technology. Here, the microarray is a component in a biochip technology assembly comprising further means for transduction, signal processing and displaying of the results.

The term "antibody" shall be understood to include polyclonal and monoclonal antibodies, any fragment thereof and genetically engineered antibodies.

The "label" can be, for example, an enzyme or a fluorescent label. A particularly preferred group of fluorescent labels is time-resolved fluorescent labels, such as lanthanide chelates. If the label is an enzyme, a substrate for said enzyme is added, wherein the subsequent reaction between the enzyme and its substrate produces a detectable signal. If the label is a fluorescent label, the excitation is carried out by radiation, for example by laser, wherein a detectable signal is created.

Preferably, all the biomarkers to be determined are proteins or peptides, each of which can be immobilised to a certain capture antibody. In this case, the labelled binders are also antibodies. Each labelled antibody is directed to an epitope of a certain biomarker, where said epitope is different from that of the epitope, which binds to the capture antibody.

A multiple of ARDS related biomarkers are simultaneously determined from the sample using a bioaffinity assay construed for example as follows: The capture binders are immobilised onto predetermined positions on the surface of a solid support, typically onto biotinylated spots or wells of a microtiter plate or the like. The capture binders will thus become arranged in the form of an array on the solid support (microtiter plate). Each capture binder is specific for a certain biomarker to be determined. Adding the sample to the array and incubating the biomarkers therein with the immobilised capture binders causes immobilising of each biomarker to the corresponding capture binder.

The detection of the biomarkers can be carried out in two ways: by a non-competitive so called "sandwich assay" or by a competitive assay. In the non-competitive assay the labelled bioaffinity components, for example labelled antibodies, are added to the plate bearing the immobilised biomarkers. After incubation and optionally removal of unbound labelled bioaffinity components, the label is excited to give a detectable signal. In this kind of assays, the strength of the signal is directly proportional to the concentration of the immobilised biomarker. The position of the "sandwich" on the microtiter plate informs which biomarker has been detected.

In the Luminex® technology, the capture antibodies are immobilised to beads, labelled with fluorescent colours so that a certain colour refers to a certain kind of capture antibodies. Upon incubation with the sample containing the biomarkers to be detected and subsequent addition of a set of second antibodies (labelled antibodies labelled with a fluorescent colour different from the bead colour) a sandwich comprising "bead-capture antibody-biomarker-labelled antibody" is formed. Each such sandwich is transported to a flow cytometer and each sandwich is classified and quantified using a dual-laser equipment.

In a competitive assay, the plate bearing the immobilised biomarkers derived from the sample is subjected to a set of labelled antigens, wherein each labelled antigen is capable of competing for the binding site on the capture binder with the corresponding immobilised biomarker derived from the sample. When the label is excited, the signal detected will be indirectly proportional to the concentration of the biomarker derived from the sample.

The invention is illustrated more in detail by reference to the drawings in which FIG. 1A shows a support (microtiter plate) with spots S1 to S5. Capture antibodies C1 to C5 have been bound to predetermined spots (FIG. 1B), which may be biotinylated to enable the binding of capture antibodies thereon. Each capture antibody is specific for a certain biomarker B1 to B5 to be determined. Upon addition of the sample to the plate shown in FIG. 1B, each capture antibody will immobilise the biomarker towards the capture antibody has been raised. Unbound biomarkers may be washed away before the addition of labelled antibodies L1 to L5, out of which one labelled antibody is specific for a certain immobilised biomarker. Upon excitation of the label L (irradiation or addition of an enzyme substrate, depending on the label L), a detectable signal is created.

Although the labelled antibody can be one single antibody bearing the necessary specificity and the label, the labelled antibody can alternatively be an assembly of primary antibody (PA) directed to the biomarker and a secondary antibody (SA), which bears the label L and binds to the Fc region of the primary antibody. See FIG. 2. This assembly avoids the expensive process of creating labelled antibodies for every biomarker one might want to detect.

When the method is repeated with samples drawn at separate points of time, the signal obtained from each labelled antibody is registered and plotted versus time (FIG. 3). For some biomarkers (B1 and B2), an increased level represents a favourable change of the patient's disease, while a decreased level of B3 and B4 also represents a favourable change. On the contrary, the decreased level of B5 represents an adverse change of the patient's disease and therefore the curve could preferably be plotted in different signs or colour so as to rapidly distinguish from the curves, which represent a favourable change.

The data from the determinations are collected into a data base, optionally together with clinical observations, therapeutic measures etc.

The invention is illustrated by the following non-restricting examples.

Example 1

In a clinical study 26 patients with ALI or ARDS were given doses of 10 microgram of interferon beta-1a for six consecutive days. This treatment reduces the mortality by 75% if compared to normal frequency observed without treatment. Serum samples derived from the patients were analyzed with respect to the following biomarkers: IL-1ra (ra=receptor antagonist), IL-6, IL-8, IL-15, Eotaxin, MCP-1 (monocyte chemotactic protein 1), MIP-1a (macrophage inflammatory protein) and CD73. In FIG. 4, a) to h) the level of each biomarker (activity for CD73) are shown as mean value for all of the patients together with the standard errors of the means (S.E.M), is plotted versus time. Day 1 refers to the value before the interferon beta administration. Day 2 refers to the value 22 hours after the first interferon beta administration; Day 3 refers to the value 22 hours after the second dose (Day 2) and so on. Day 7 represents the levels 22 hours after the last administration of interferon beta. FIG. 4 shows that the level of the biomarkers IL-1ra, IL-6, IL-8, IL-15 and MCP-1 decreased rapidly with time, i.e. with recovery of the patients. On the other hand, the soluble CD73 activity (nmol/mL/hr) increased until Day 9 i.e. two days after the last dose, followed by a decrease towards the baseline values. The level of the biomarkers Eotaxin and MIP-1a also increased with time, i.e. with recovery of the patients.

Example 2

Soluble CD73 activity was measured from samples of one of the treated patients in the above mentioned study at indicated time points (see FIG. 5) using the previously published thin layer chromatography based technique. This patient showed very strong induction in the soluble CD73 activity. The soluble CD73 concentration was measured by an ELISA assay based on the use of a capture antibody and a detection antibody in a sandwich assay. The activity and concentration of the soluble CD73 were measured from aliquots of the same samples. FIG. 5 shows that the soluble CD73 activity and concentration behave similarly.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

The invention claimed is:

1. A method for the treatment of a patient suffering from acute respiratory distress syndrome (ARDS), the method comprising:
    obtaining a serum sample from the patient at a first point in time before administering interferon beta;
    treating the patient with interferon beta during a treatment period;
    obtaining a serum sample from the patient at a later point in time during the treatment period; and
    determining a change in the levels and/or activities of three biomarkers and optionally an additional one to five biomarkers in the serum sample obtained at the first point in time compared to the levels and/or activities of the biomarkers in the serum sample obtained at the later point in time; and
wherein the treatment of the patient with interferon beta is continued when the biomarkers each discontinue showing a favorable change, or start to show an unfavorable change;
    wherein the three biomarkers are CD73, IL-6 and human eotaxin-1 (CCL11) and wherein
the one to five additional biomarkers are selected from the group consisting of interleukin-1 receptor antagonist (IL-1 ra), interleukin-8 (IL-8), interleukin-15 (IL-15), monocyte chemoattractant protein-1 (MCP-1), and macrophage inflammatory protein (MIP-1a).

2. The method according to claim 1, wherein the level and/or activity of CD73 is decreased in the sample obtained at the later point in time compared to the sample obtained at the first point in time.

3. The method according to claim 1, wherein (IL-lra) is selected as a biomarker, and the level and/or activity of IL-1ra is increased in the sample obtained at the later point in time compared to the sample obtained at the first point in time.

4. The method according to claim 1, wherein the level and/or activity of IL-6 is increased in the sample obtained at the later point in time compared to the sample obtained at the first point in time.

5. The method according to claim 1, wherein IL-8 is selected as a biomarker, and the level and/or activity of IL-8 is increased in the sample obtained at the later point in time compared to the sample obtained at the first point in time.

6. The method according to claim 1, wherein IL-15 is selected as a biomarker, and the level and/or activity of IL-15 is increased in the sample obtained at the later point in time compared to the sample obtained at the first point in time.

7. The method according to claim 1, wherein MCP-1 is selected as a biomarker, and the level and/or activity of MCP-1 is increased in the sample obtained at the later point in time compared to the sample obtained at the first point in time.

8. The method according to claim 1, wherein the level and/or activity of eotaxin is decreased in the sample obtained at the later point in time compared to the sample obtained at the first point in time.

9. The method according to claim 1, wherein the biomarkers further comprise all of IL-1ra, IL-8, IL-15, MCP-1, and macrophage inflammatory protein (MIP-1a).

10. The method according to claim 1, wherein the change in the levels and/or activities of the biomarkers is determined using a microarray.

11. The method according to claim 1, wherein the change in the levels and/or activities of the biomarkers is determined using a multiplex assay.

12. The method according to claim 1, wherein the change in the levels and/or activities of the biomarkers is determined using an antibody microassay.

13. The method according to claim 1, wherein the change in the levels and/or activities of the biomarkers is determined using a bead-based immunoassay system.

14. The method according to claim 1, wherein the change in the levels and/or activities of the biomarkers is determined using a reporter cell line.

15. The method according to claim 1, wherein the activity of CD73 is determined using thin layer chromatography.

\* \* \* \* \*